(12) United States Patent
Yamada

(10) Patent No.: US 8,199,880 B2
(45) Date of Patent: Jun. 12, 2012

(54) RADIOGRAPHIC APPARATUS AND IMAGING METHOD THEREOF

(75) Inventor: Naoki Yamada, Soka (JP)

(73) Assignee: Canon Kabushiki Kaisha, Tokyo (JP)

( * ) Notice: Subject to any disclaimer, the term of this patent is extended or adjusted under 35 U.S.C. 154(b) by 161 days.

(21) Appl. No.: 12/766,333

(22) Filed: Apr. 23, 2010

(65) Prior Publication Data

US 2010/0290592 A1    Nov. 18, 2010

(30) Foreign Application Priority Data

May 18, 2009   (JP) .................................. 2009-120394

(51) Int. Cl.
*H05G 1/56*        (2006.01)
(52) U.S. Cl. ........................................................ 378/114
(58) Field of Classification Search .................... 378/62, 378/110, 114
See application file for complete search history.

(56) References Cited

U.S. PATENT DOCUMENTS

| | | | |
|---|---|---|---|
| 7,433,446 B2 * | 10/2008 | Abe | 378/114 |
| 7,686,512 B2 * | 3/2010 | Spahn | 378/207 |
| 2008/0037708 A1 * | 2/2008 | Kuzmanovic | 378/62 |

FOREIGN PATENT DOCUMENTS

JP    2004-105356    4/2004

* cited by examiner

*Primary Examiner* — Irakli Kiknadze
(74) *Attorney, Agent, or Firm* — Cowan, Liebowitz & Latman, P.C.

(57) ABSTRACT

There is provided a technology that enables an operator to designate whether or not to continue imaging if divided capture has been interrupted in a radiographic apparatus. During continuation of divided capture, the state of an irradiation switch for designating irradiation of radiation is detected by an irradiation switch state detection unit. When a suspension of the designation of irradiation of radiation has been detected, information indicating continuation of imaging, performing of imaging again, or cancellation of imaging is presented to an operator, thereby preventing an unintended interruption of imaging.

28 Claims, 18 Drawing Sheets

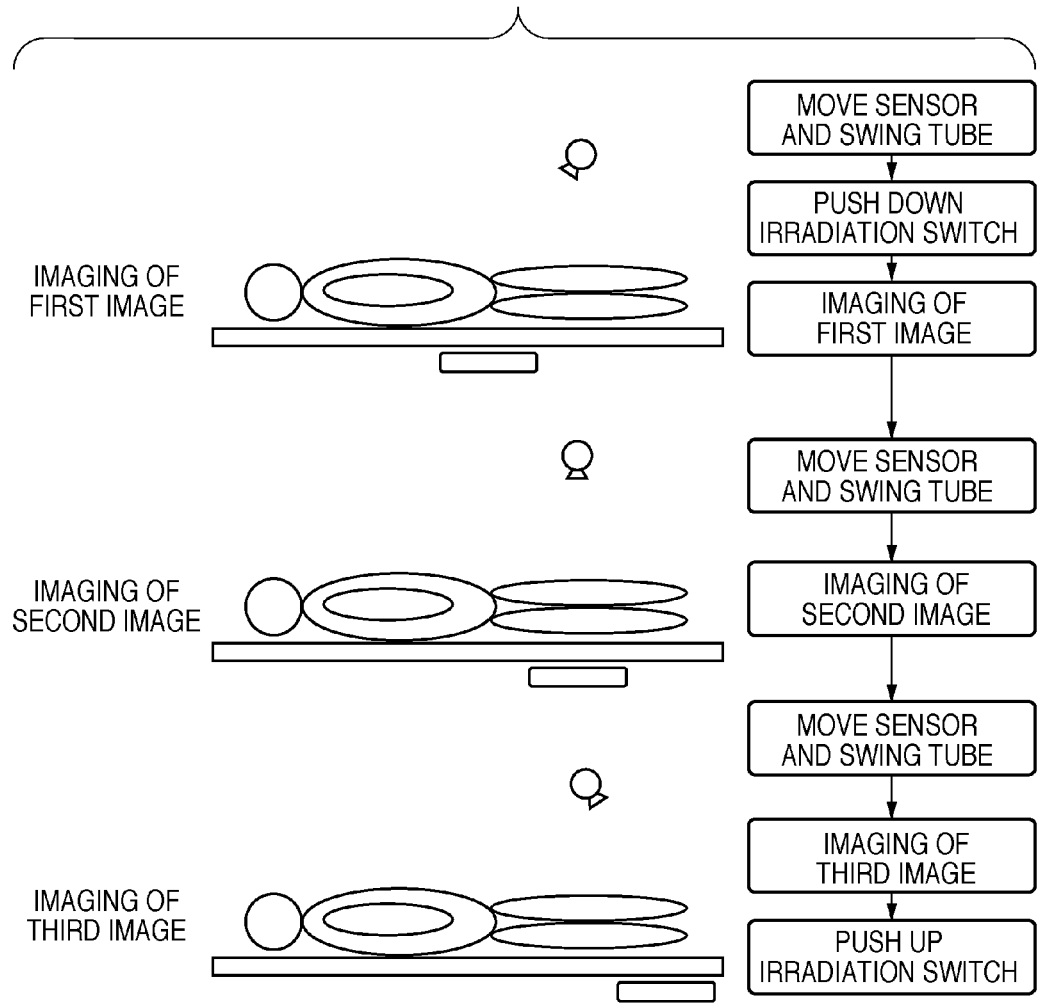
F I G. 1

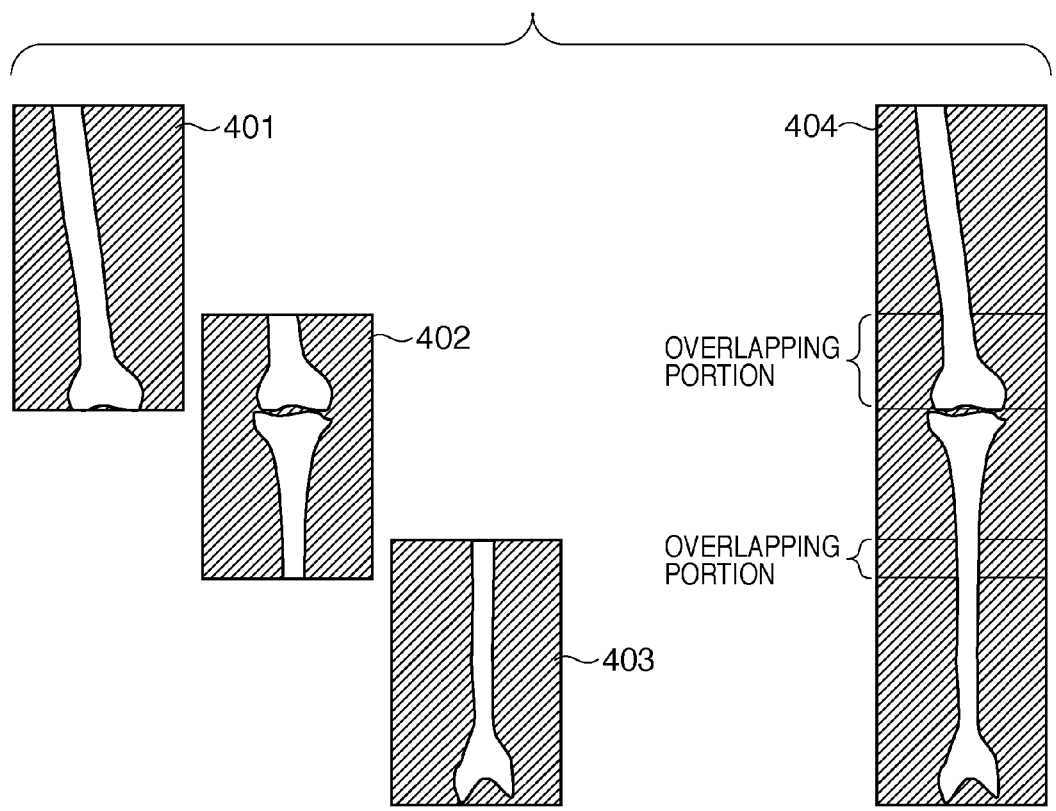
F I G. 4

35cm

43cm

701

0°

702

90°

F I G. 11
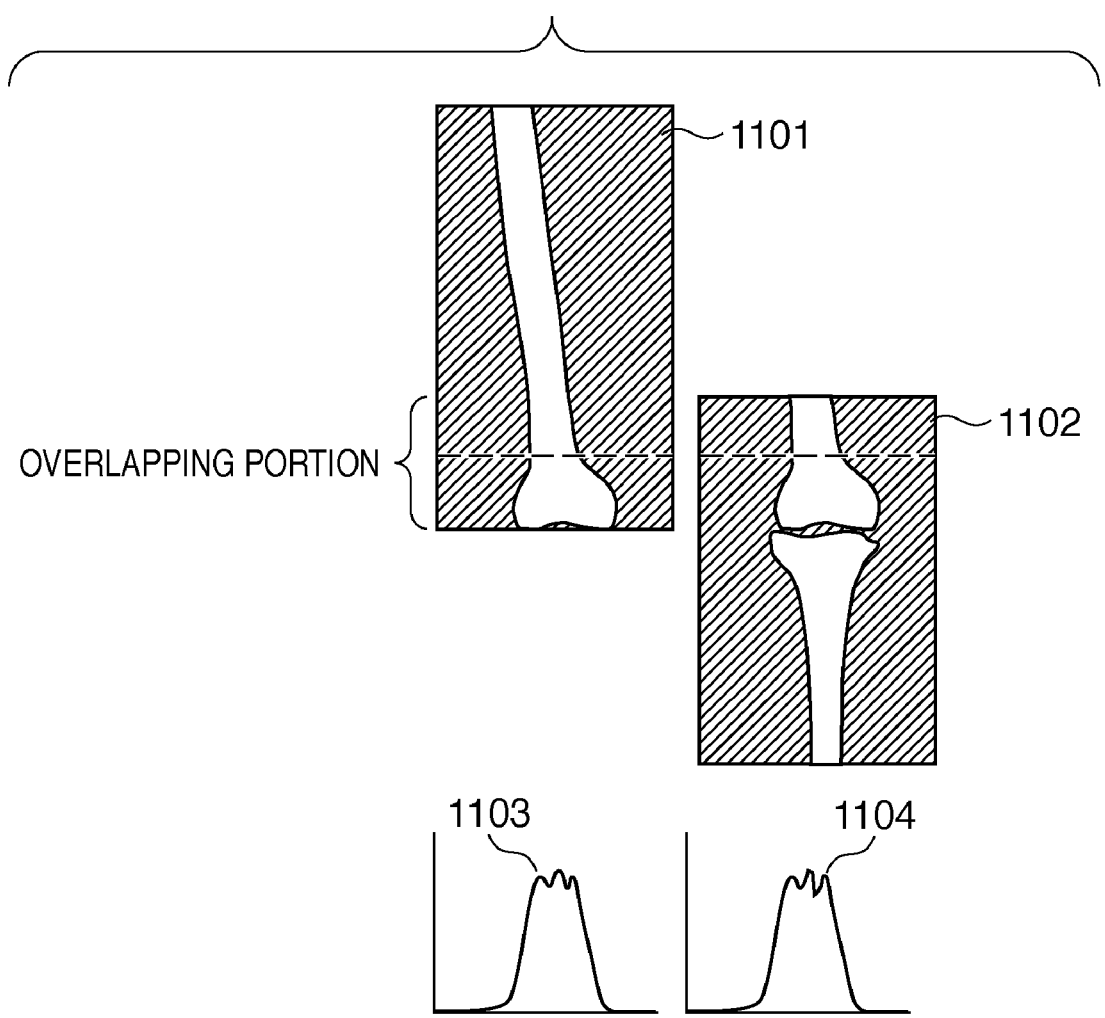

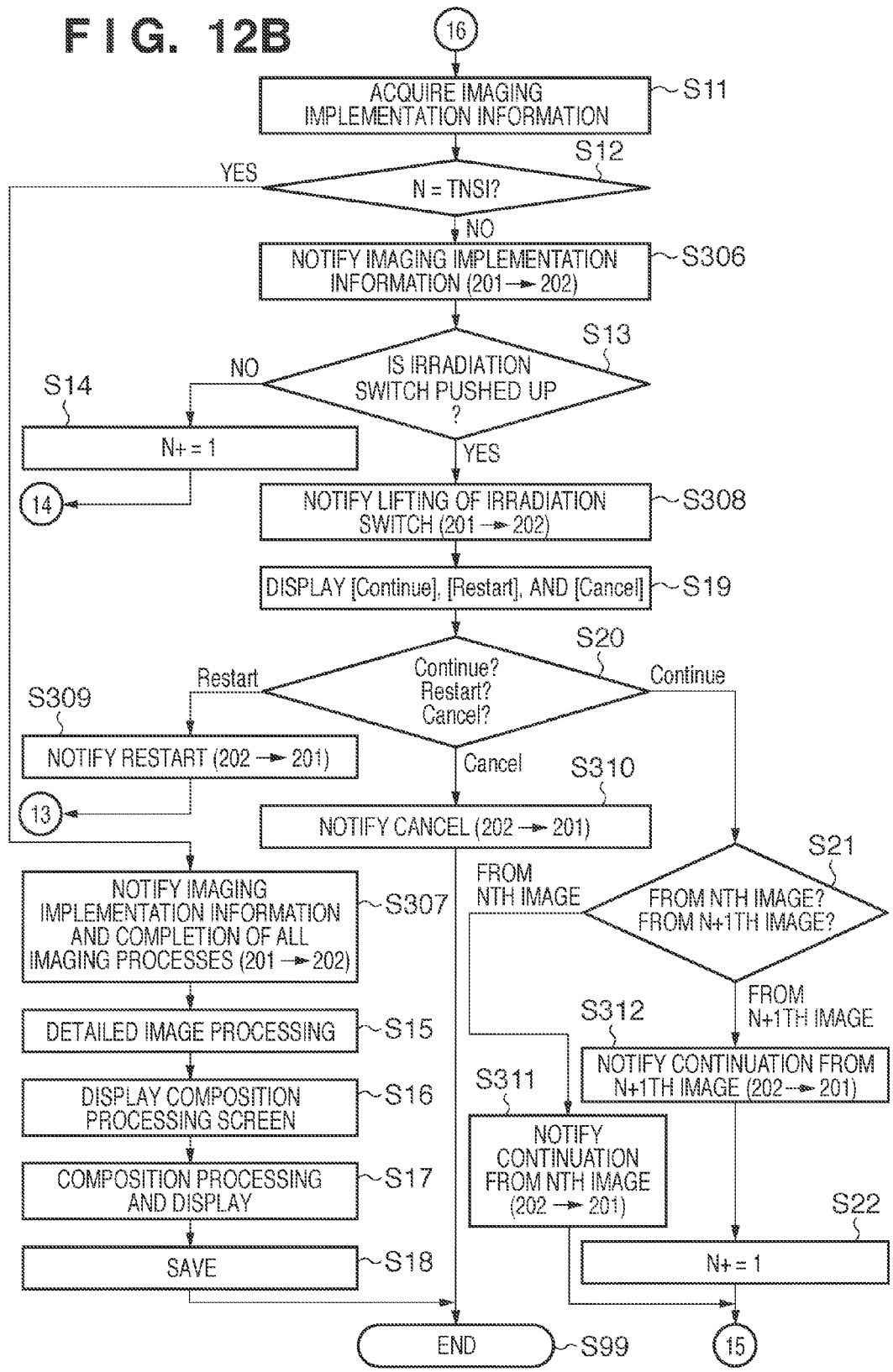

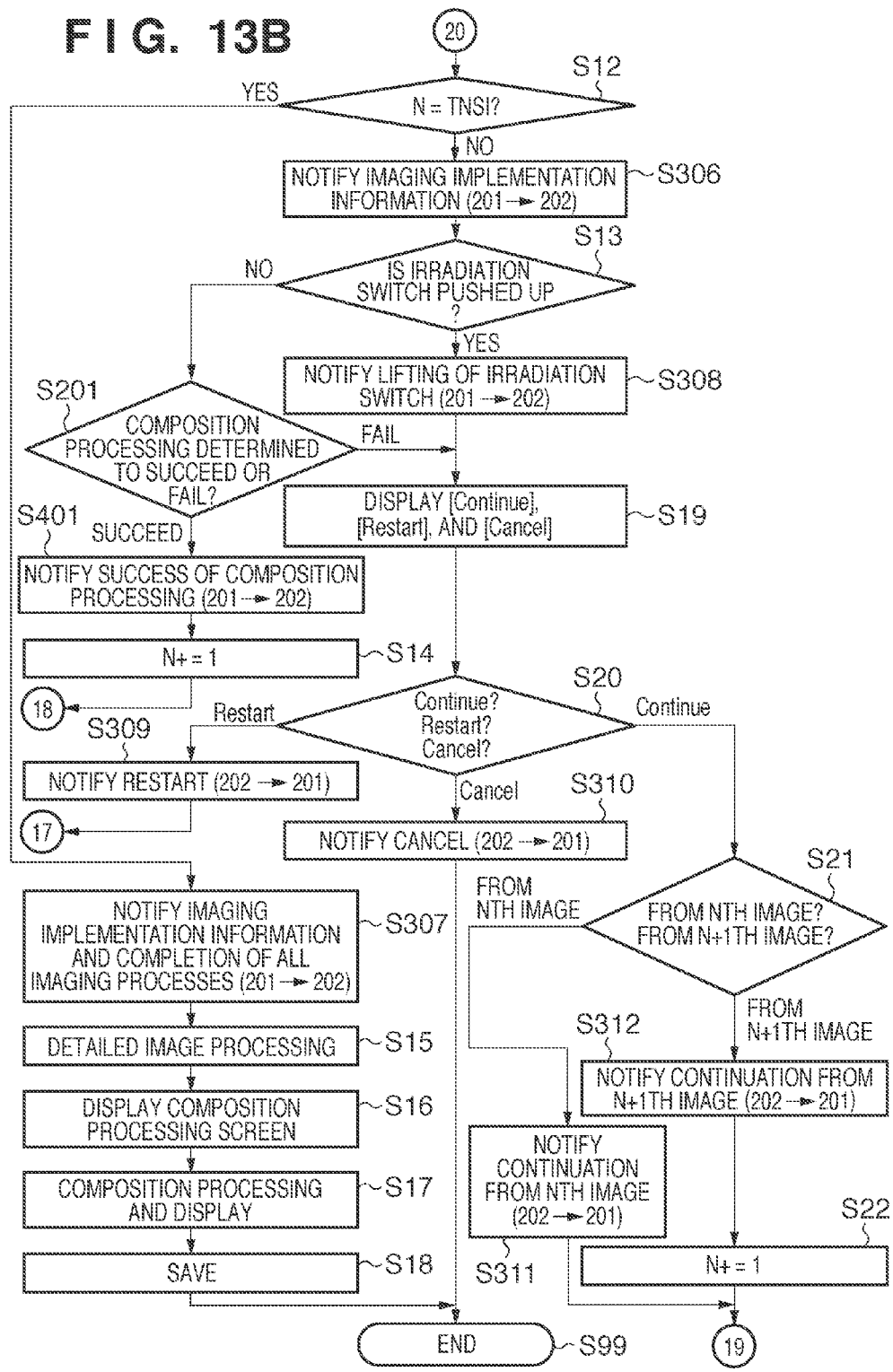

RADIOGRAPHIC APPARATUS AND IMAGING METHOD THEREOF

BACKGROUND OF THE INVENTION

1. Field of the Invention

The present invention relates to a radiographic apparatus and a radiographic method for obtaining a radiation image of an object by irradiation of radiation, and particularly relates to a technology for a method in which the same object is imaged in a plurality of imaging processes.

2. Description of the Related Art

Conventionally, imaging using radiation has been used in various fields, and particularly in the medical field, is one of the most important methods for diagnosis. In recent years, an imaging sensor that collects, as digitized image data, a radiation image obtained by radiography has also been put into practical use, and digitization is underway in the radiography field. In general, the larger type of such imaging sensors predominantly has a size of about 43 cm×43 cm.

When radiography is performed using such an imaging sensor, there are cases where an area larger than the imaging sensor (for example, the whole body or the full lower limb) has to be imaged. In such cases, it is not possible to image the entire area by a single imaging process, so imaging is performed in a plurality of divided imaging processes. An imaging method has been established in which a desired single piece of large image data is obtained by performing composition processing for multiple pieces of image data acquired by each imaging process. Such an imaging method is generally called divided capture, long-length imaging, stitch capture, or the like.

As a document describing the above imaging method, a reference can be made to Japanese Patent Laid-Open No. 2004-105356.

Here, a general example of a divided capture method will be described.

FIG. 1 is a diagram showing an example in which an image of the full lower limb is acquired from three divided images. First, before performing imaging, the position of an imaging sensor and the swing angle of a tube that generates radiation are adjusted, and preparation for imaging for the first image is performed. In this example, the position of the imaging sensor and the swing angle of the tube during each imaging process are assumed to be determined prior to the positional adjustment.

After performing the positional adjustment, a radiation irradiation switch is depressed by an operator, and the first divided image is imaged. Upon completion of the imaging of the first divided image, the position of the imaging sensor and the swing angle of the tube are automatically adjusted as preparation for imaging of the second image. At this time, the operator continues depressing the radiation irradiation switch. Then, after performing the positional adjustment, the second divided image is imaged. Thereafter, imaging is completed up to the third image by the same operation, and finally the operator depresses the irradiation switch, whereby the series of divided capture is completed.

After performing such divided capture, the acquired three pieces of divided image data are composed by image processing, thus obtaining a single desired composite image. Then, the composite image obtained is put to use in diagnosis, for example, by being displayed or printed.

However, when divided images are obtained in the above-described manner, there have been situations where imaging cannot be completed normally up to the third image if the object moves during imaging, or if the operator releases the irradiation switch. When such a situation occurs, it has been hitherto common to stop all the imaging processes once, and perform imaging again from the first image. Accordingly, it has cost twice the labor for the operator to perform imaging again from the first image, and this has also caused an object to undergo unnecessary exposure to radiation. The present invention provides a technology that enables the operator to designate whether or not to continue imaging if divided capture has been interrupted in a radiographic apparatus.

SUMMARY OF THE INVENTION

In order to solve the above-described problems, the present invention provides an irradiation switch for designating irradiation of radiation; an irradiation switch state detection unit for detecting the state of the irradiation switch; a radiation irradiation unit for generating radiation and apply the radiation to an object, in accordance with the state of the irradiation switch; an image capturing unit for detecting the radiation applied by the radiation irradiation unit, and outputting as image data; a radiographic imaging table for placing the object; a movement control unit for moving one or more of the radiation irradiation unit, the image capturing unit, and the radiographic imaging table; an imaging control unit for controlling information required for radiography; a storage unit adapted to store the image data and imaging information; an image processing unit for performing image processing for the image data; a display unit adapted to display, for example, the image data and information relating to imaging; and a display control unit for controlling the content displayed in the display unit.

The present invention enables the operator to designate whether or not to continue imaging if divided capture has been interrupted. Accordingly, it is possible to avoid generating twice the labor for the operator, and also prevent an object from undergoing unnecessary exposure to radiation.

Further features of the present invention will become apparent from the following description of exemplary embodiments (with reference to the attached drawings).

BRIEF DESCRIPTION OF THE DRAWINGS

FIG. 1 is a diagram showing an example in which an image of the full lower limb is acquired from three divided images.

FIG. 4 is a diagram showing an example of divided images used when performing divided capture, and an example of a composite image thereof.

FIG. 11 is a diagram showing an example of a method for determining whether composition processing succeeds or fails.

FIGS. 12A and 12B are flowcharts illustrating a flow of a divided capture method in Embodiment 4.

FIGS. 13A and 13B are flowcharts illustrating a flow of a divided capture method of the present invention in Embodiment 5.

DESCRIPTION OF THE EMBODIMENTS

Hereinafter, embodiments of the present invention will be described with reference to the drawings.

Figure 2:
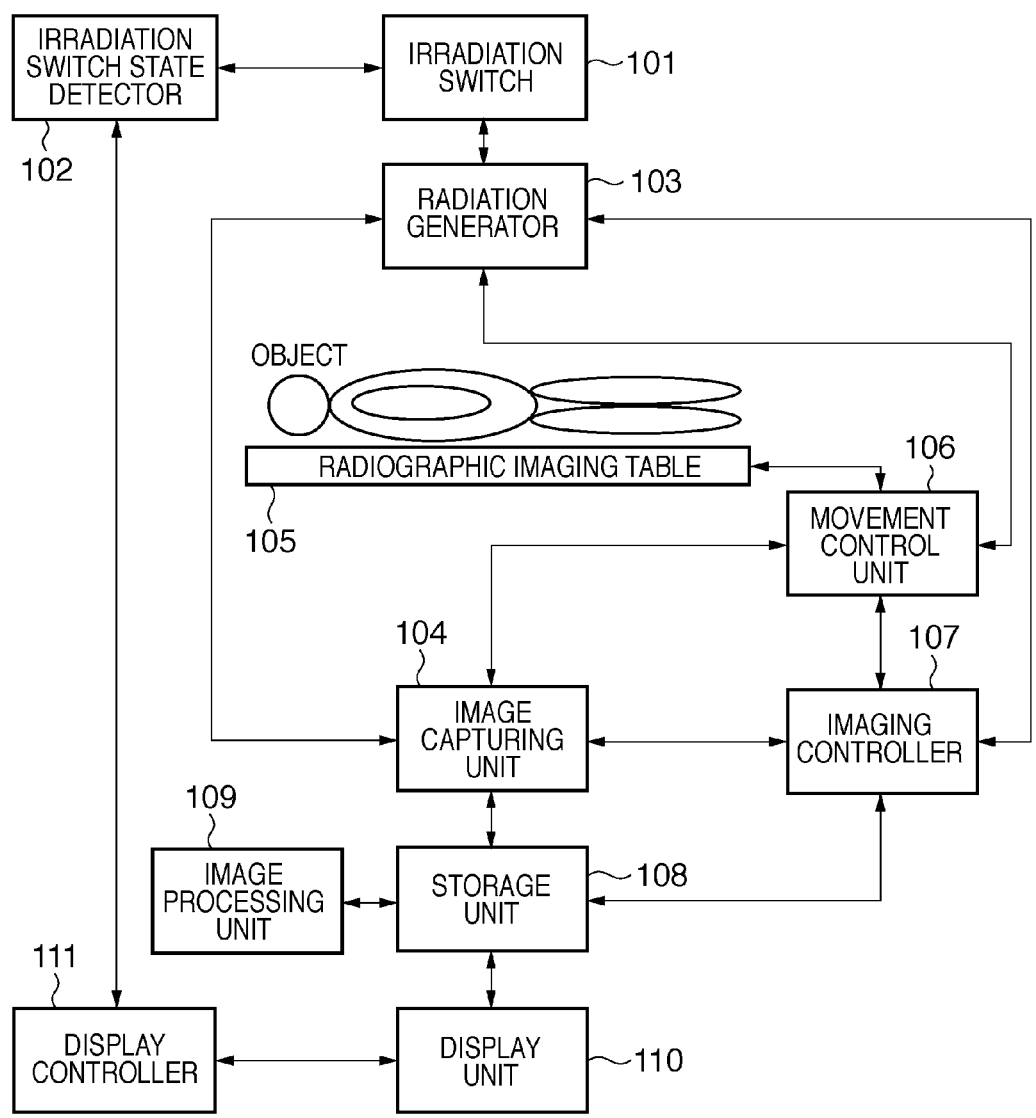
FIG. 2 is a block diagram showing a configuration of a radiographic apparatus according to Embodiment 1.

FIG. 2 is a block diagram showing a configuration of a radiographic apparatus according to the present invention.

Figure 3:
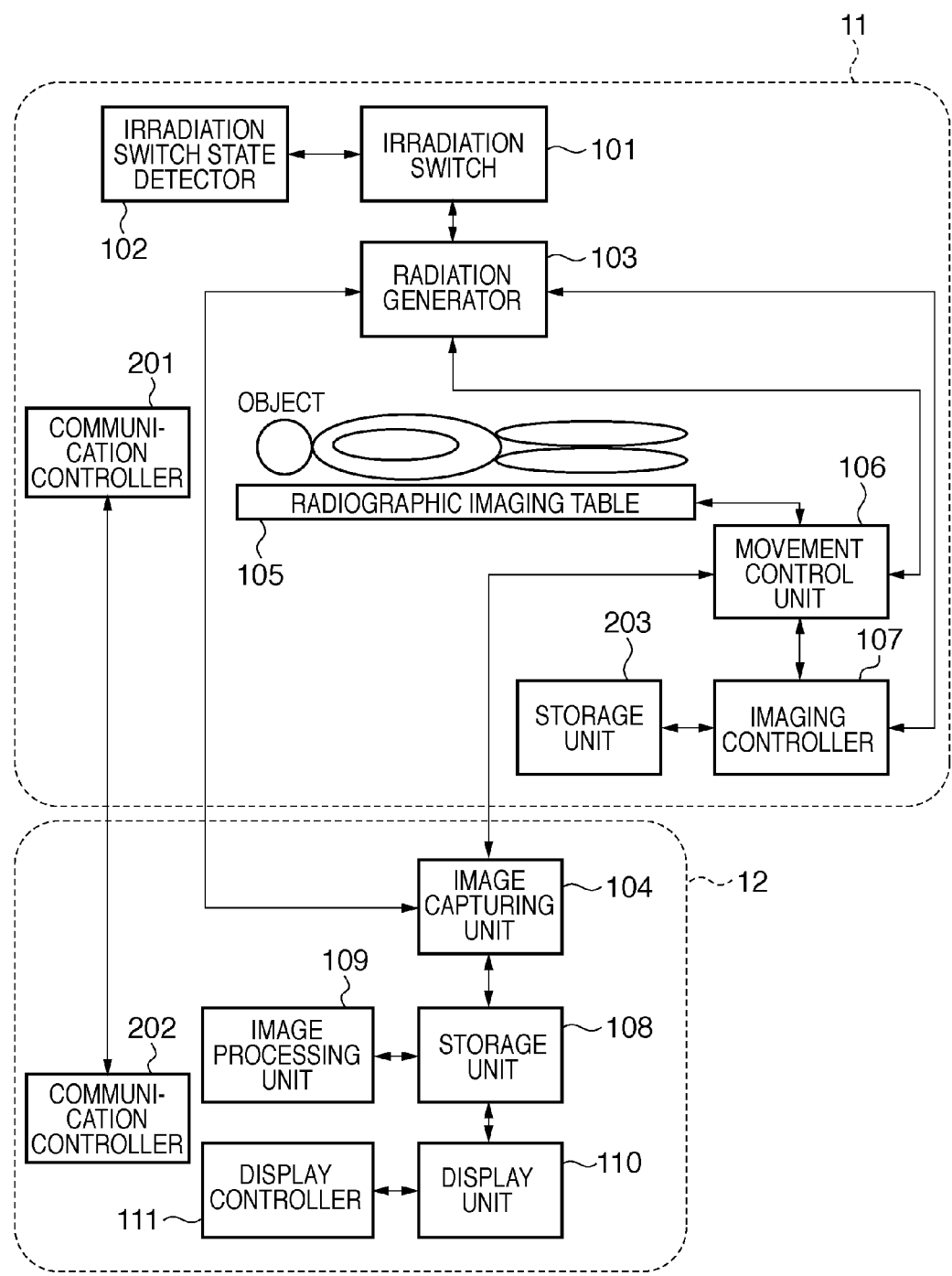
FIG. 3 is a block diagram showing a configuration for the case where the radiographic apparatus according to Embodiment 1 is divided into a radiation generating apparatus and an imaging and display apparatus.

FIG. 3 is a block diagram showing a configuration in which the radiographic apparatus according to the example shown in FIG. 2 is divided into a radiation generating apparatus 11 and an imaging and display apparatus 12. In the following, the configuration thereof will be described with reference to FIGS. 2 and 3.

An irradiation switch 101 provides a designation to generate radiation when depressed by the operator. An irradiation switch state detector 102 detects the state of the irradiation switch 101. Here, the irradiation switch state detector 102 detects the pushed down state (on-state) and the pushed up state (off-state).

A radiation generator 103 serving as a radiation irradiation unit applies radiation, in accordance with a designation from the irradiation switch 101. Specifically, the radiation generator 103 includes a high voltage generator that generates a high voltage required for irradiation of radiation and a tube shown in FIG. 1.

An image capturing unit 104 serving as an image capturing means images radiation applied from the radiation generator 103. That is, the radiation applied from the radiation generator 103 passes through an object, and the transmitted radiation is detected and imaged by the imaging unit 104, and is output as image data of the radiation.

A radiographic imaging table 105 is used for placing an object during radiography. Specifically, the radiographic imaging table 105 may be an upright stand used when imaging is performed in an upright position, or a supine table used when imaging is performed in a supine position, for example.

A movement control unit 106 serving as a placement adjusting unit adjusts the placement of each of the radiation generator 103, the image capturing unit 104, and the radiographic imaging table 105. For example, the movement control unit 106 adjusts the swing angle of the radiation generator 103 during divided capture, and also adjusts the position of the image capturing unit 104. Furthermore, the radiographic imaging table 105 can be moved vertically and horizontally.

An imaging controller 107 serving as an imaging control unit controls imaging performed by divided capture in the present invention. Specifically, the imaging controller 107 performs calculation of the total number of stitching images (TNSI) required for divided capture, control of the number of captured images during imaging, determination of imaging information such as imaging conditions corresponding to the relevant number of captured image, and acquisition of implementation information after imaging, and so on.

A storage unit 108 serving as a storage means stores image data that has been imaged by the image capturing unit 104. Specifically, the storage unit 108 uses, for example, a temporary storage device such as a RAM (Random Access Memory), or a storage device such as an HDD (Hard Disk Drive).

An image processing unit 109 serving as an image processing means performs, for example, composition processing for divided images or display processing for displaying captured image data. That is, here, the image data stored in the storage unit 108 is subjected to image processing by the image processing unit 109, and the image data that has been subjected to image processing is also stored in the same storage unit 108.

Here, an example of composition processing performed by the image processing unit 109 will be described.

FIG. 4 is a diagram showing an example of divided images used when performing divided capture, and an example of a composite image thereof. When the first to third captured images as a plurality of captured images are acquired while switching the image sensing area for the object as shown in FIG. 1, three divided images as indicated by 401 to 403 in FIG. 4 are acquired. The image processing unit 109 composes these three divided images, thereby generating a single composite image 404. Examples of a method of composition processing performed by the image processing unit 109 include a method in which the image processing unit 109 analyzes the overlapping portion of each of the divided images and composes coordinates that substantially geometrically match each other, and a method in which a marker is copied to the overlapping portion during imaging and the marker is detected for performing composition processing. In the present invention, however, no specific reference is made to methods of composition processing.

A display unit 110 serving as a display means also serves as a user interface unit. The display unit 110 displays, for example, the image data stored in the storage unit 108, a notification indicating an interruption of acquisition of captured images, and buttons for accepting designations from a user that is an operator. A display controller 111 serving as a display control unit controls the content displayed in the display unit 110.

Note that the functional blocks 101 to 111 that have been described thus far are portions common to FIGS. 2 and 3. In addition to these functional blocks, a communication controller 201 that serves as a first communication control unit and is provided in the radiation generating apparatus 11, a communication controller 202 that serves as a second communication control unit and is provided in the imaging and display apparatus 12, and a storage unit 203 are present in FIG. 3.

The communication controller 201 and the communication controller 202 transmit to/receive from each other information present in the radiation generating apparatus and information present in the imaging and display apparatus, respectively, and notify each other of these pieces of information, before or after imaging. The storage unit 203 stores, for example, information related to imaging.

The following describes a specific imaging method for improving the continuity of divided capture using the above-described configuration.

Embodiment 1

In Embodiment 1, a description will be given of a divided capture method in the configuration shown in FIG. 2.

Figure 5A:
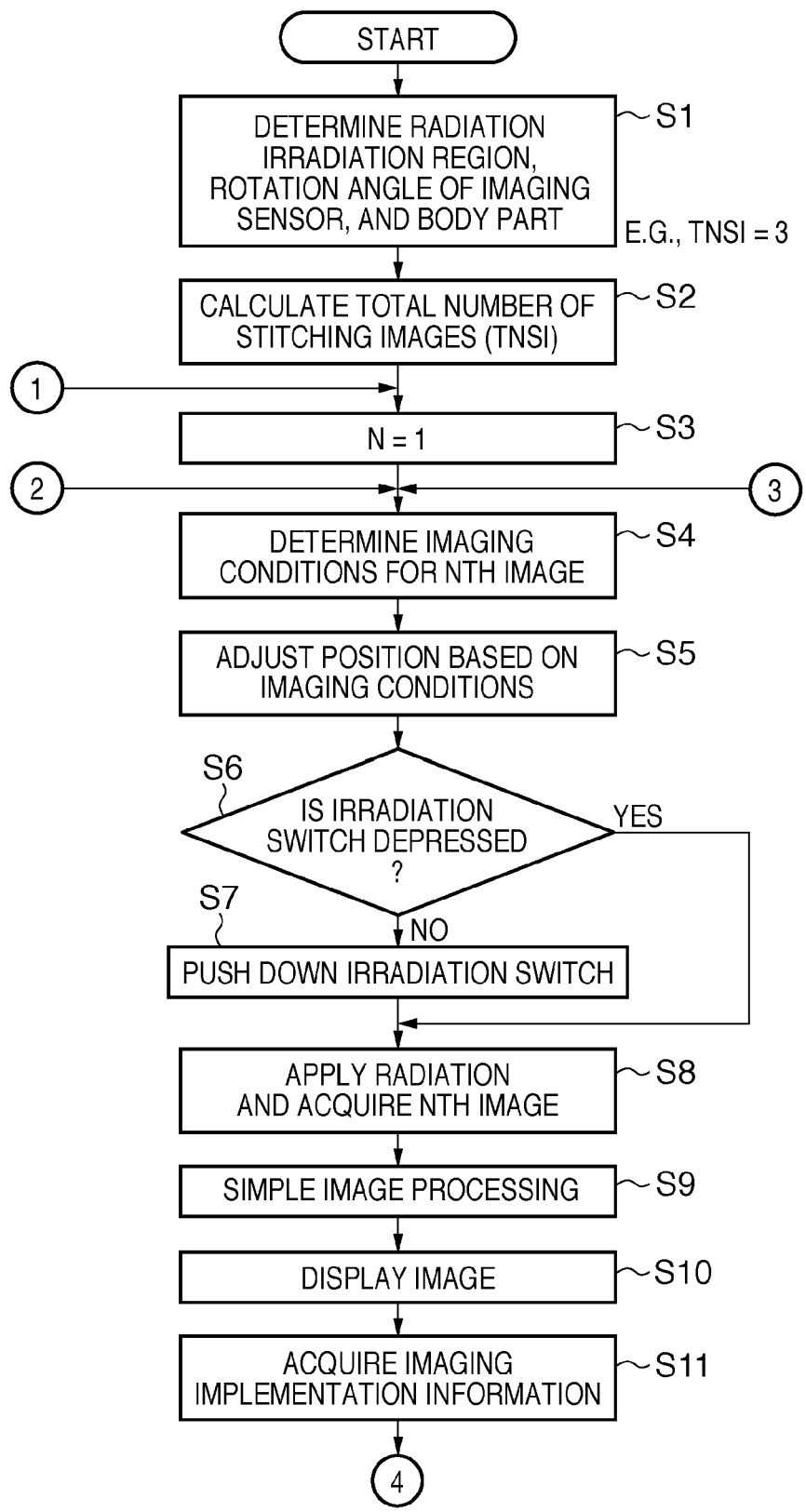
FIGS. 5A and 5B are flowcharts illustrating a flow of a divided capture method in the configuration of Embodiment 1.
Figure 5B:
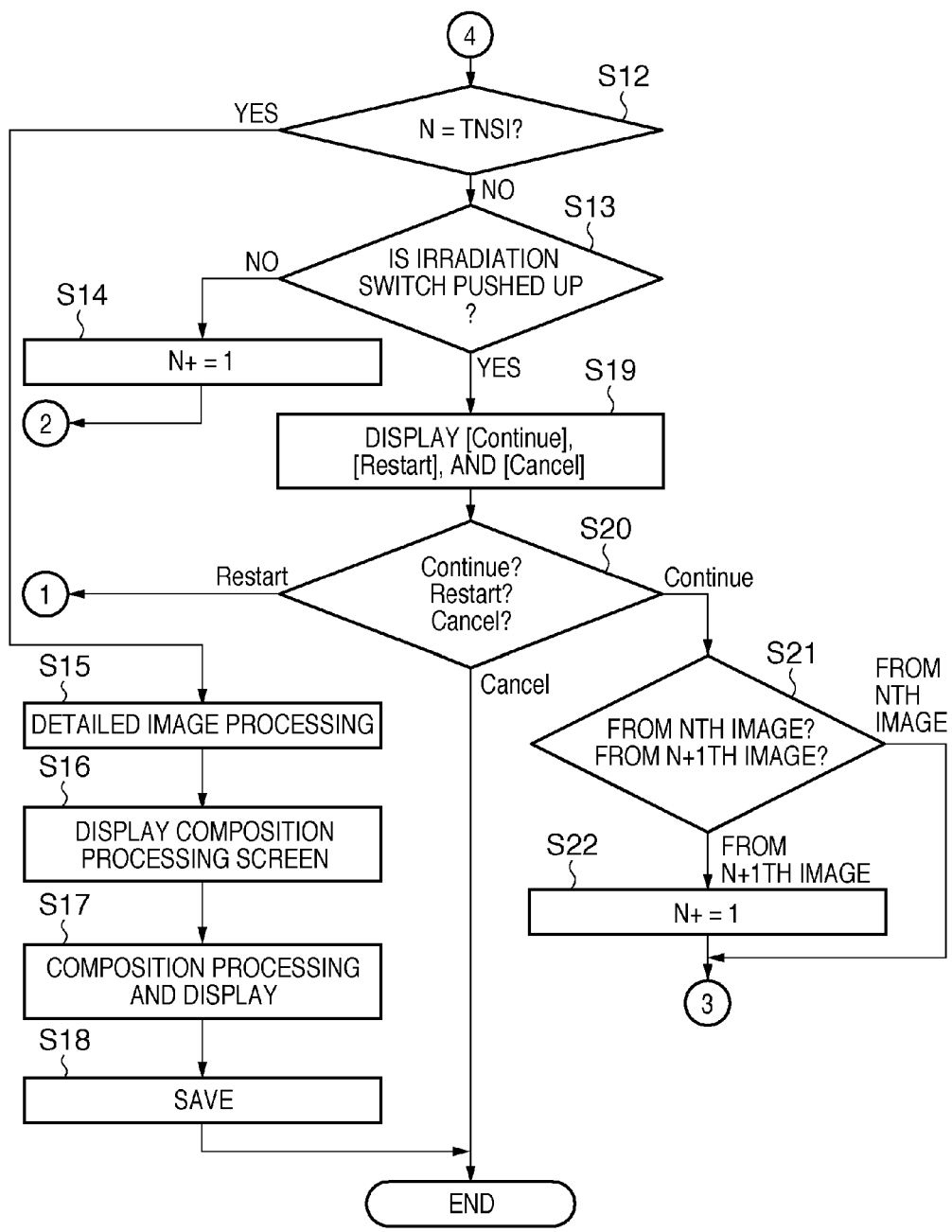

FIGS. 5A and 5B are flowcharts illustrating a flow of a divided capture method of the present invention in the configuration shown in FIG. 2.

Figure 6:
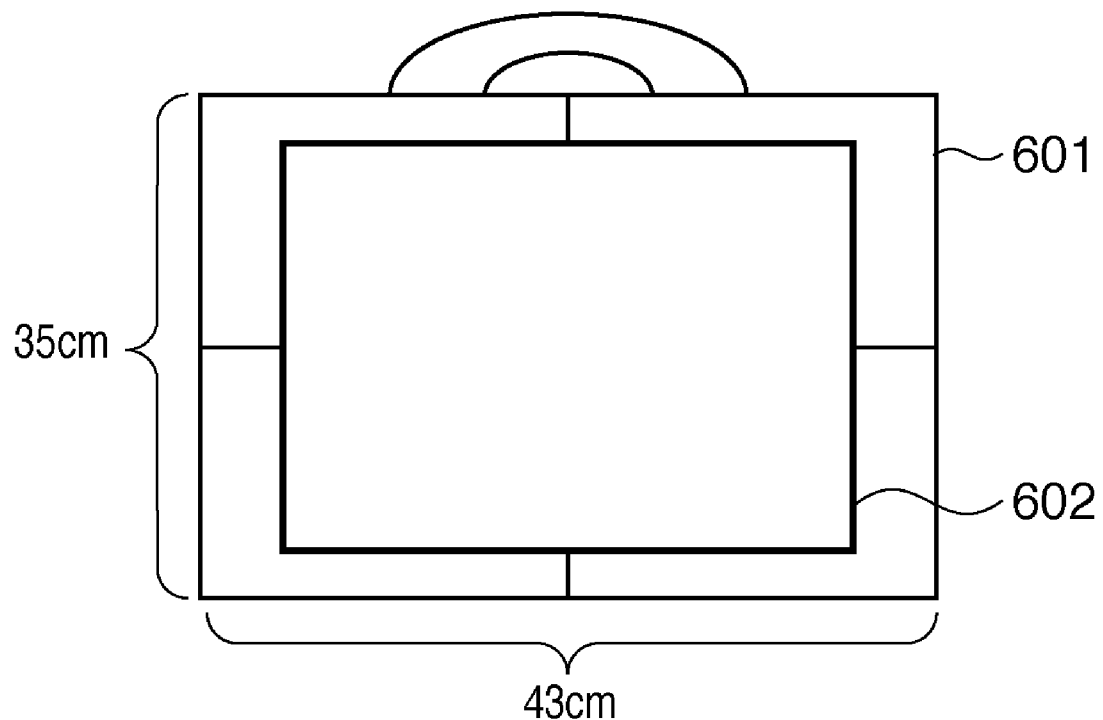
FIG. 6 is a diagram illustrating a radiation irradiation region.

FIG. 6 is a diagram illustrating a radiation irradiation region.

First, in step S1, placement conditions including a radiation irradiation region for an object and the rotation angle of an imaging sensor with respect to the axis of the object, and a plurality of body parts divided for the object are determined in accordance with a designation from the operator.

Here, the imaging sensor serving as the image capturing means will be described.

FIG. 6 is a diagram illustrating a radiation irradiation region. As shown in FIG. 6, a radiation irradiation region 602 is located at the central portion of an imaging sensor 601. When radiography is performed, an actual irradiation region is narrowed by a device called a collimator. Accordingly, even if the imaging sensor 601 has a size of 35 cm×43 cm, the region that is actually irradiated with radiation is smaller like the region represented by the irradiation region 602. This setting has to be made prior to imaging.

Next, the rotation of the imaging sensor will be described.

Figure 7:
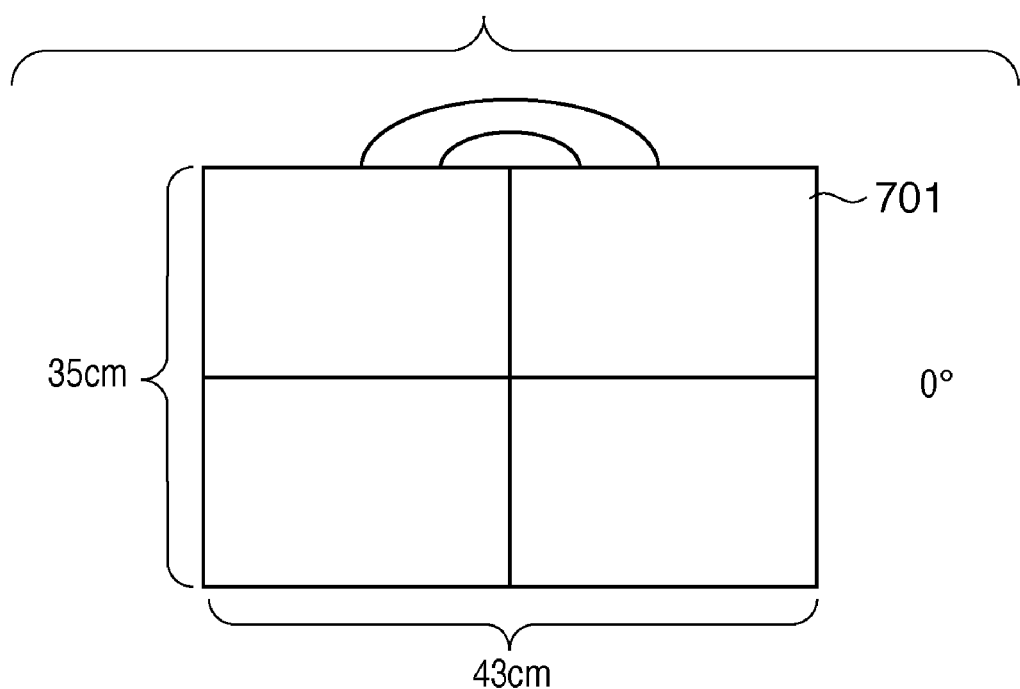
FIG. 7 is a diagram illustrating rotation of an imaging sensor.
Figure 7:
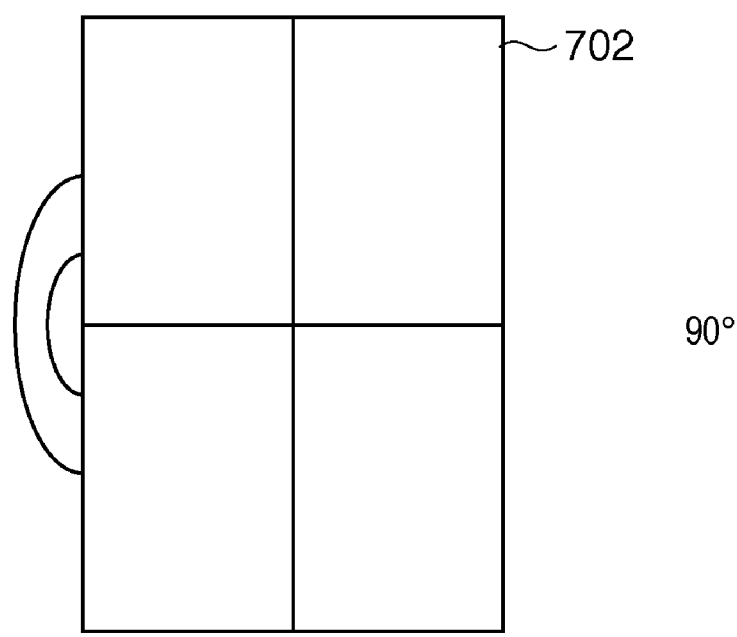

FIG. 7 is a diagram illustrating rotation of an imaging sensor. FIG. 7 shows an example in which the rotation angle of an imaging sensor 701 is 0°, and the rotation angle of an imaging sensor 702 is 90°. When divided capture is performed, all the imaging processes are not necessarily performed with the same rotation angle, depending on the length of the body part. That is, there may be cases where the first and second images are imaged with a rotation angle of 0° (701), and only the third image is imaged with a rotation angle of 90° (702). This rotation angle setting is determined prior to imaging.

In step S2 in FIG. 5A, the total number of stitching images (TNSI) required to successively capture a plurality of divided images in sequence is calculated by the imaging controller 107. The imaging controller 107 determines the total number of stitching images (TNSI) based on the information of the irradiation region, of the rotation angle of the imaging sensor, and of the body part designated in step S1.

In step S3, a capturing number N indicating an index of the number of captured images is initialized to 1.

In step S4, the imaging controller 107 reads the imaging conditions corresponding to the Nth image from the storage unit 108.

After the imaging conditions corresponding to the Nth image have been determined, in step S5, the movement control unit 106 adjusts the position of the radiation generator 103 and the image capturing unit 104 based on the imaging conditions.

Next, in step S6, the irradiation switch state detector 102 detects the current state of the irradiation switch 101. If the irradiation switch 101 is in the pushed up state (off-state), indicating an interruption of designation of irradiation of radiation, the process moves to step S7. If the irradiation switch 101 is already in the pushed down state (on-state), indicating a continuation of irradiation of radiation, the process moves to step S8. Here, supposing that the current state is the pushed up state (off-state), the process moves to step S7.

In step S7, the operator pushes down the irradiation switch 101, bringing the switch into the on-state.

In step S8, the radiation generator 103 actually applies radiation, and the image capturing unit 104 acquires the Nth image data. The acquired image data is stored in the storage unit 108.

In step S9, the image processing unit 109 performs display image processing for the Nth image data stored in the storage unit 108, and the image data that has undergone the image processing is stored in the storage unit 108 again. However, in this embodiment, the display image processing performed during imaging is limited to simple processing. One reason is that detailed image processing is required to display an image suitable for diagnosis, and such processing is time-consuming. The simple image processing as mentioned herein is minimal processing required for display, such as processing of correcting the properties of the imaging sensor and gradation conversion processing.

In step S10, the display controller 111 reads, from the storage unit 108, the image data that has undergone the simple image processing in step S9, and the image data is displayed in the display unit 110. From this display, the operator can check the Nth image data obtained by imaging.

Then, in step S11, the imaging controller 107 acquires imaging implementation information. The imaging implementation information includes, for example, the values of the tube voltage and the tube current required for radiography, the irradiation region set in step S1, the rotation angle of the imaging sensor, and the like.

In step S12, the imaging controller 107 compares the value of N with the value of the total number of stitching images (TNSI), and determines whether or not these values match each other. If they match each other, this means that all the imaging processes have been completed, so the process moves to step S15. If the irradiation switch 101 is still in the pushed down state (on-state), the process moves to step S14. If the irradiation switch 101 is in the pushed up state (off-state) even though all the imaging processes have not yet been completed, the process moves to step S19.

In step S13, the irradiation switch state detector 102 determines the current state of the irradiation switch 101 again. In step S14, the imaging controller 107 adds 1 to N indicating the index of the number of captured images, and the process returns to step S4.

In step S15, the image processing unit 109 performs detailed image processing, and the process moves to step S16.

In step S16, the display controller 111 causes a composition processing screen to be displayed in the display unit 110. That is, for the image data displayed on the screen for generating a single composite image after all the imaging processes have been completed, detailed image processing suitable for diagnosis is performed by the image processing unit 109, unlike the simple processing performed in step S9. Here, the detailed image processing includes noise-reduction processing for reducing random noise in an image, highlight processing for highlighting edges and contrast, and the like, in addition to the simple image processing performed in step S9.

Then, after the composition processing screen is displayed in step S16, in step S17, the image processing unit 109 performs composition processing as shown in FIG. 4, whereby a desired single composite image is generated.

In step S18, the generated composite image is stored in the storage unit 108. Upon completion of saving of the composite image, the process moves to step S99 and divided capture ends.

In step S19, since the irradiation switch 101 is brought into the pushed up state (off-state), in other words, the switch has turned off even though imaging for the total number of stitching images has not been completed, a display for allowing the user to determine whether or not to continue the operation of acquiring the captured images is provided. More specifically, the display controller 111 provides a display in the display unit 110 for allowing the operator, in other words, the user to continue imaging, perform imaging again from the beginning, or cancel imaging.

Figure 8:
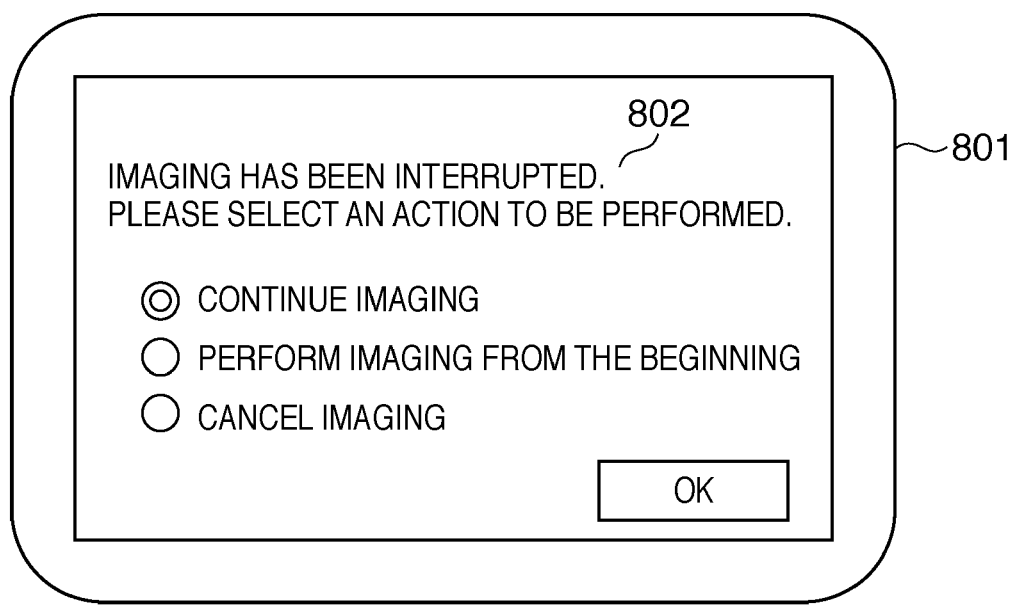
FIG. 8 is a diagram showing an example of a screen displayed in a display unit 110.

FIG. 8 is a diagram showing an example of a screen displayed in the display unit 110. In FIG. 8, the displayed content 802 of a display unit 801 is caused to be displayed by the display controller 111. The operator can proceed to the next processing by selecting to continue imaging, perform imaging again from the beginning, or cancel imaging from this displayed content, and depressing an OK button. More specifically, if "Continue imaging" is selected, this corresponds to Continue in step S20, and the process moves to step S21. If "Perform imaging again from the beginning" is selected, this corresponds to Restart (restart measurement) in step S20, and the process returns to step S3. If "Cancel imaging" is selected, the process moves to step S99 and imaging ends. In FIG. 8, the displayed content for which selection is made using radio buttons is shown as an example. However, the displayed content according to the present invention is not limited thereto.

If "Continue" is selected in step S20, the process moves to step S21.

In step S21, the display controller 111 causes the content indicating that imaging will be continued from the Nth image or that imaging will be continued from N+1th image to be displayed in the display unit 110, and makes an inquiry to the operator again. Note that this inquiry may be performed simultaneously with provision of a display in step S19. If "Continue from Nth image" is selected in step S21, the process returns to step S4. If "Continue from N+1th image" is selected, 1 is added to N in step S22, and the process returns to step S4.

By performing this series of steps, even if the irradiation switch 101 is brought into the pushed up state (off-state) during divided capture and imaging has been interrupted, it is possible to continue the imaging from any image number desired by the operator.

Embodiment 2

In Embodiment 2, an example will be described in which the number of times imaging implementation information indicating implementation of each imaging process has been acquired is used as a condition for determining whether or not all the imaging processes have been completed, unlike Embodiment 1 in which the index of the number of captured images is used as a condition for determining whether or not all the imaging processes have been completed.

Figure 9A:
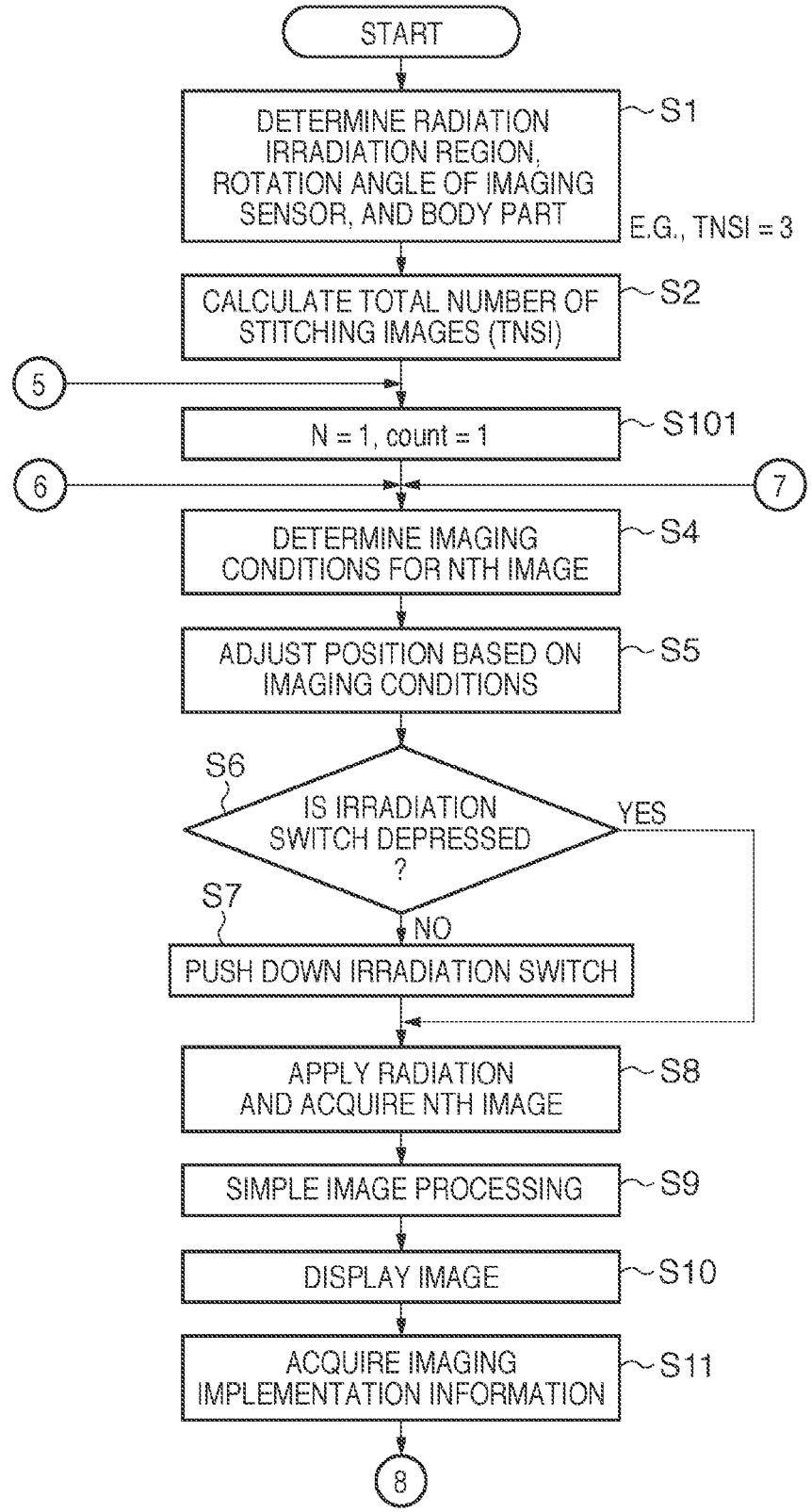
FIGS. 9A and 9B are flowcharts illustrating a flow of a divided capture method of the present invention in Embodiment 2.
Figure 9B:
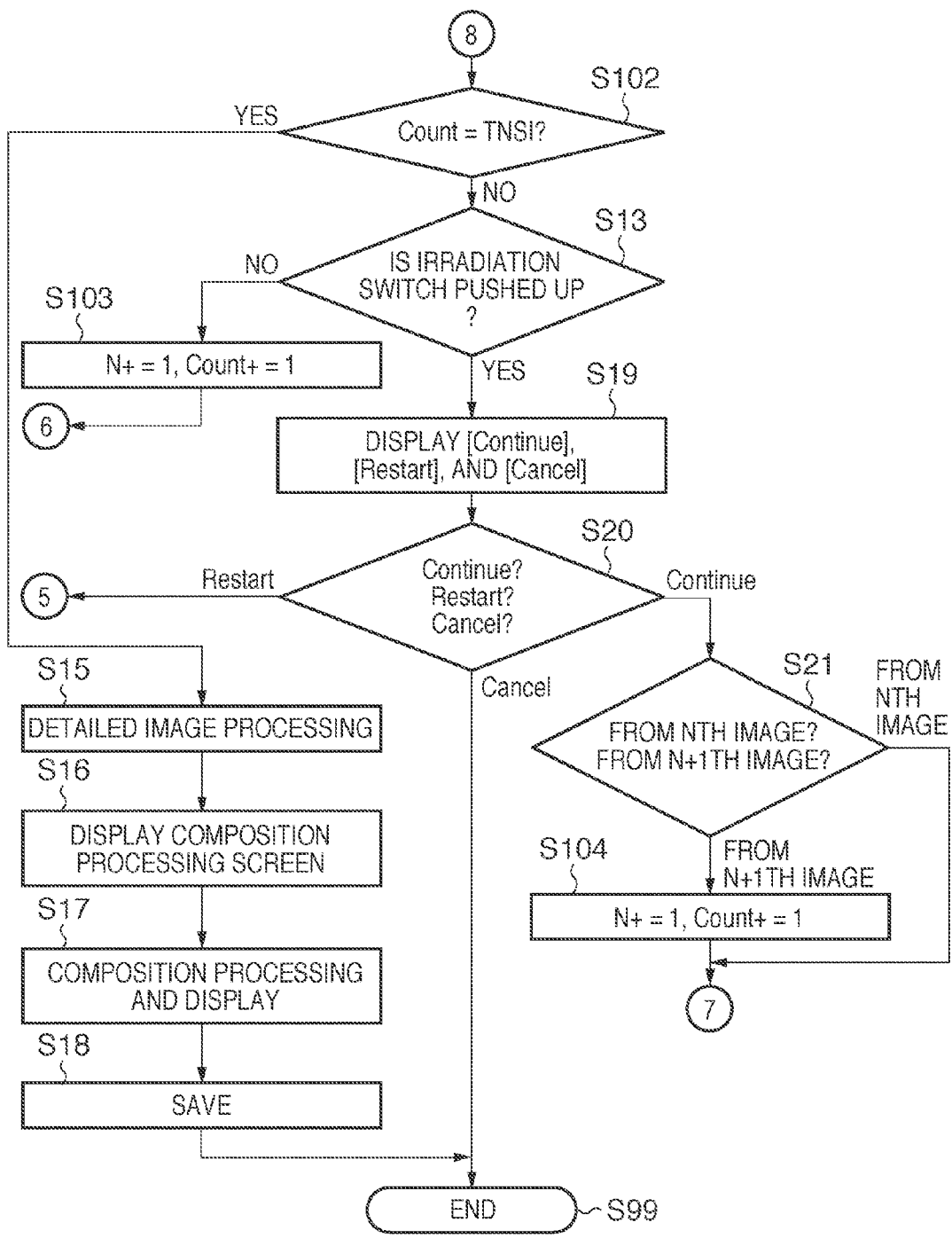

FIGS. 9A and 9B are flowcharts illustrating a flow of a divided capture method of the present invention in Embodiment 2. In FIGS. 9A and 9B, the details of the steps other than steps S101 to S104 are the same as those of the steps described in relation to FIGS. 5A and 5B, so the description thereof has been omitted here.

In step S101, the count value (Count) indicating the number of times the imaging implementation information has been acquired is initialized to "1".

In step S102, the imaging controller 107 compares the count value with the value of the total number of stitching images (TNSI), and determines whether or not these values match each other. If they match each other, this means that all the imaging processes have been completed, so the process moves to step S15. If they do not match each other, it is necessary to continue imaging, so the process moves to step S13.

In addition, "1" is added to the count in step S103 and step S104.

As described thus far, according to Embodiment 2, not only "N" indicating the index of the number of captured images, but also the count of the number of times the imaging implementation information has been acquired can be used to determine whether or not all the imaging processes have been completed.

Embodiment 3

In Embodiment 3, a description will be given of a divided capture method that takes into account the case where the object has moved during imaging in the configuration shown in FIG. 2.

Figure 10A:
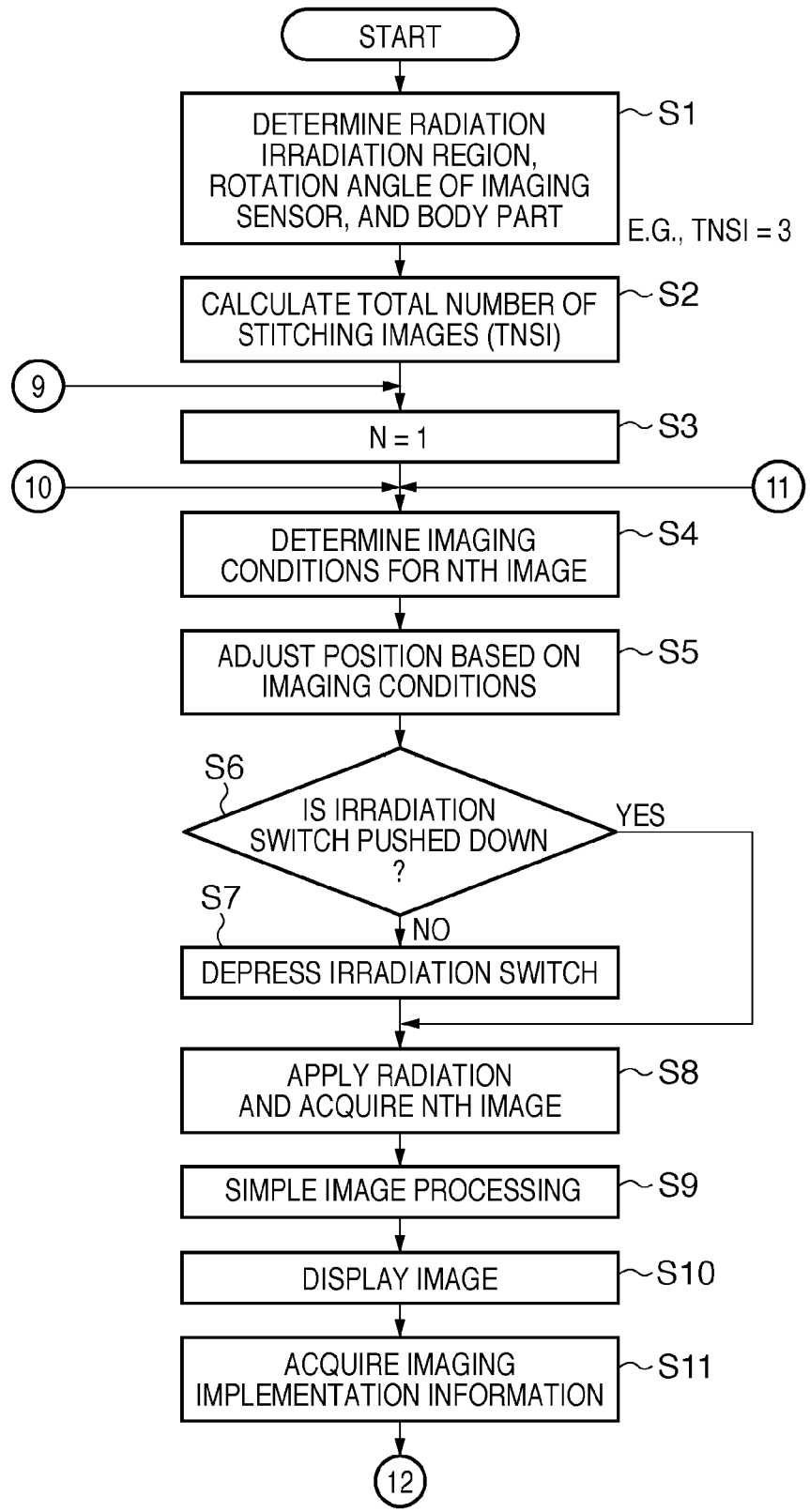
FIGS. 10A and 10B are flowcharts illustrating a flow of a divided capture method of the present invention in Embodiment 3.
Figure 10B:
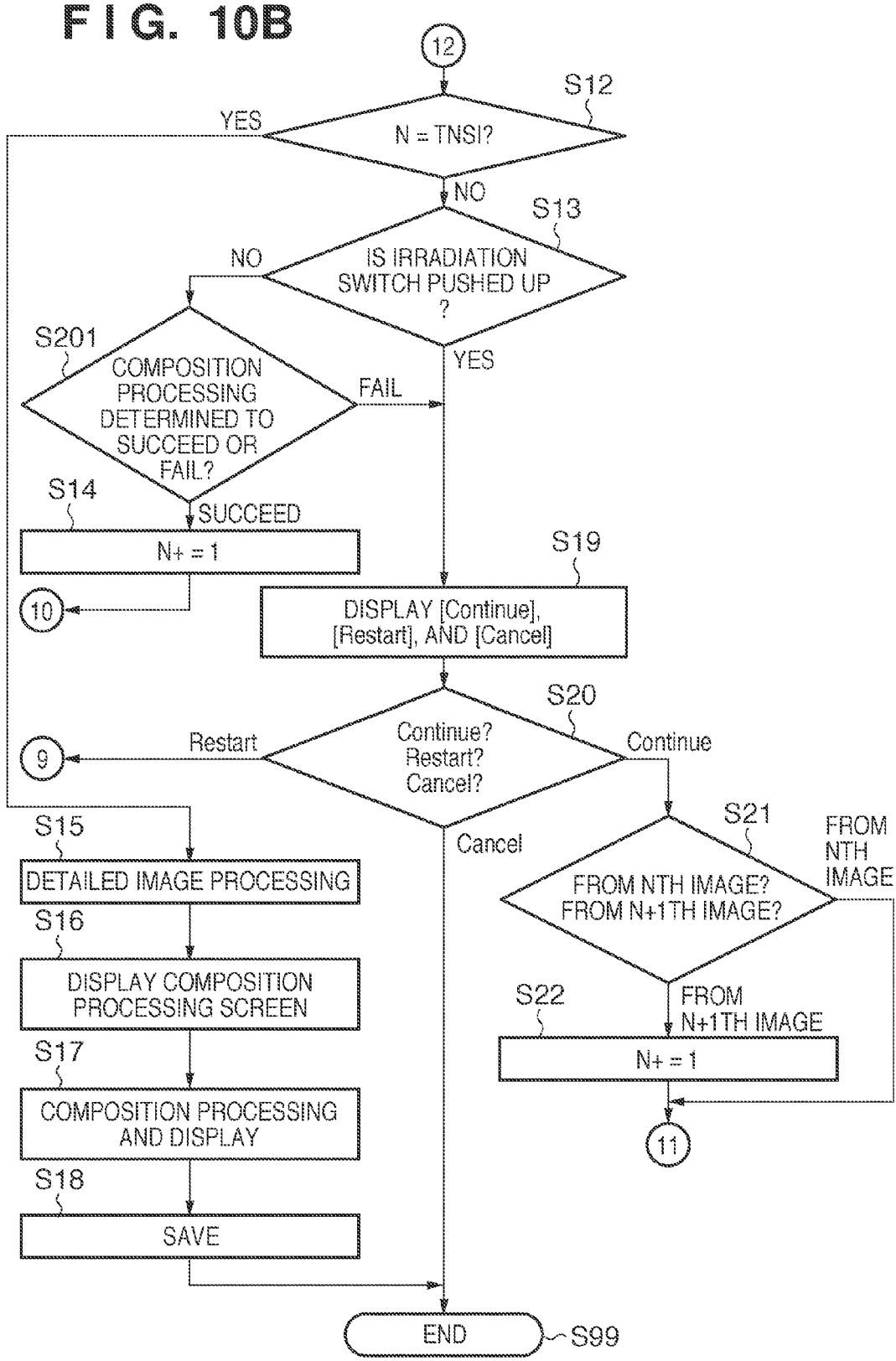

FIGS. 10A and 10B are flowcharts illustrating a flow of a divided capture method of the present invention in Embodiment 3. In FIGS. 10A and 10B, the details of the steps other than S201 are the same as those of the steps described in relation to FIGS. 5A and 5B, so the description thereof has been omitted here.

In step S201, the image processing unit 109 determines whether or not composition processing can be performed for each imaging process. That is, if the object has moved during imaging an image, the image cannot be successfully composed during the later composition processing; accordingly, in Embodiment 3, each of the plurality of divided images is composed for each imaging process, the degree of matching between the divided images is calculated, and whether or not the degree of matching falls within a specific threshold level, in other words, whether or not composition processing can be performed is determined. If it is determined that composition processing succeeds, the process moves to step S14. On the other hand, if it is determined that composition processing fails, the process moves to step S19.

Here, an exemplary method for determining whether composition processing succeeds or fails will be described. FIG. 11 is a diagram showing an example of a method for determining whether composition processing succeeds or fails. In FIG. 11, a divided image 1101 corresponds to the first divided image in FIG. 1, and a divided image 1102 corresponds to the second divided image in FIG. 1. A histogram 1103 is the histogram at the dotted line portion of the divided image 1101, and a histogram 1104 is the histogram at the dotted line portion of the divided image 1102. In this example, the histogram is checked for only a single location of the overlapping dotted line portion, but the histogram may be checked for a plurality of locations.

The image processing unit 109 uses the histograms 1103 and 1104 as a method for determining whether composition processing succeeds or fails. That is, the histograms of the overlapping portions are calculated during composition processing. If the degree of matching between the histograms is low and does not fall within a specific threshold level (for example, in the case where as a result of comparing the pixel values on the histograms and counting the number of the pixels having a difference of ±100 or greater, the number count is large), it is determined that composition processing will fail even if it is performed.

Adding such processing enables the operator to determine whether or not the later composition processing fail during imaging, when the object has moved. If it is determined that composition processing fails, it is possible to cope with the movement of the object by adjusting the position of the object so as to attain the degree of matching required for composition processing, and continuing the imaging process from the captured image for which imaging was interrupted.

Embodiment 4

In Embodiment 4, a description will be given of a divided capture method in the configuration of the radiographic apparatus shown in FIG. 3. In this embodiment, the communication controllers 201 and 202 are installed for the radiation generating apparatus 11 and the imaging and display apparatus 12, respectively, thereby providing these apparatuses with a function of communicating with each other. With this communication function, the apparatuses can transmit to/receive from each other information indicating, for example, which of the total number of captured images is being currently imaged during imaging the plurality of captured images, and can perform more reliable imaging by checking that information.

Figure 12A:
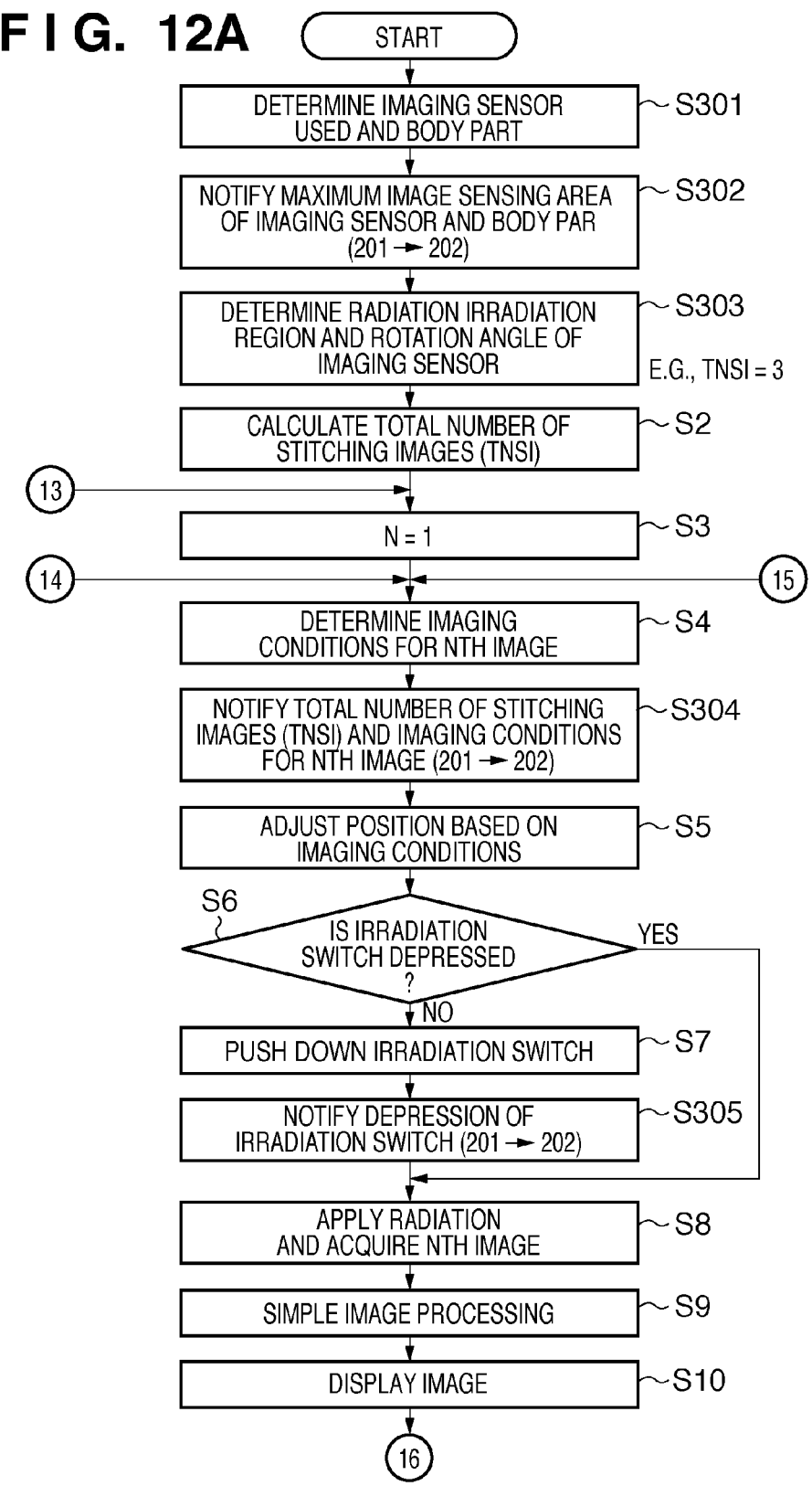

FIGS. 12A and 12B are flowcharts illustrating a flow of a divided capture method in Embodiment 4 in the configuration shown in FIG. 3. In FIGS. 12A and 12B, the details of the steps other than steps S301 to S312 are the same as those of the steps of FIGS. 5A and 5B, so the description thereof has been omitted here.

In step S301, the operator determines the imaging sensor used for the present divided capture and the body part, based on the content displayed in the display unit 110. Then, in step S302, the imaging controller 107 causes the communication controller 202 to notify the communication controller 201 of the information of the maximum image sensing area of the imaging sensor used and of the body part. Through this notification, the information of the maximum image sensing area of the imaging sensor and of the body part determined in the imaging and display apparatus is conveyed to the radiation generating apparatus. Note that a maximum image sensing area refers to the largest area that can be imaged by the imaging sensor, that is, the size of the imaging sensor.

In step S303, the imaging controller 107 determines the irradiation region that is actually irradiated with radiation and the rotation angle of the imaging sensor, based on the conditions notified in step S302. In step S2, the imaging controller 107 calculates the total number of stitching images (TNSI) based on these conditions.

In step S304, the imaging controller 107 causes the communication controller 201 to notify the communication controller 202 of the total number of stitching images (TNSI) and the imaging condition for the Nth image that have been determined in step S2 and step S4, respectively. Through this notification, the total number of stitching images (TNSI) and the imaging condition for the Nth image that have been determined in the radiation generating apparatus are conveyed to the imaging and display apparatus. Note that in step S4, the imaging controller 107 reads the imaging condition for the Nth image from the storage unit 203.

In step S305, the imaging controller 107 causes the communication controller 201 to notify the communication controller 202 of the state of the irradiation switch 101 that has been detected by the irradiation switch state detector 102. Through this notification, the pushed down state (on-state) of the irradiation switch 101 that has been detected in the radiation generating apparatus is conveyed to the imaging and display apparatus, whereby the imaging and display apparatus can know that irradiation of radiation will be started.

In step S306, the imaging controller 107 causes the communication controller 201 to notify the communication controller 202 of the acquired imaging implementation information. Through this notification, the imaging implementation information acquired in the radiation generating apparatus is conveyed to the imaging and display apparatus.

In step S307, if all the imaging processes have been completed, the imaging controller 107 causes the communication controller 201 to notify the communication controller 202 of the implementation information for the last imaging process and information indicating completion of all the imaging processes. Through this notification, the imaging and display apparatus can know that all the imaging processes have succeeded, so detailed image processing can be performed by the image processing unit 109, and the composition processing screen can be displayed in the display unit 110.

In step S308, the imaging controller 107 causes the communication controller 201 to notify the communication controller 202 of the state of the irradiation switch 101 that has been detected by the irradiation switch state detector 102. Through this notification, the imaging and display apparatus can know that the irradiation switch has been pushed up even though all the imaging processes have not been completed, so the display controller 111 provides a display for the operator to determine whether to continue imaging, perform imaging again from the beginning, or cancel imaging.

If "Perform imaging again from the beginning" is selected in the display unit 110, in step S309, the imaging controller 107 causes the communication controller 202 to notify the communication controller 201 of the information indicating this.

If "Cancel imaging" is selected in the display unit 110, in step S310, the imaging controller 107 causes the communication controller 202 to notify the communication controller 201 of the information indicating this.

If "Continue imaging from Nth image" is selected in the display unit 110, in step S311, the imaging controller 107 causes the communication controller 202 to notify the communication controller 201 of the information indicating this.

If "Continue imaging from N+1th image" is selected in the display unit 110, in step S312, the imaging controller 107 causes the communication controller 202 to notify the communication controller 201 of the information indicating this. Through these notifications, the radiation generating apparatus can know the content selected in the display unit 110, and can continue imaging from any desired image number, based on the notified information.

It should be appreciated that according to the present invention, the implementation details described in Embodiment 2 can also be applied to the configuration shown in FIG. 3.

Embodiment 5

In Embodiment 5, a description will be given of a divided capture method that takes into account the case where the object has moved during imaging in the configuration shown in FIG. 3.

Figure 13A:
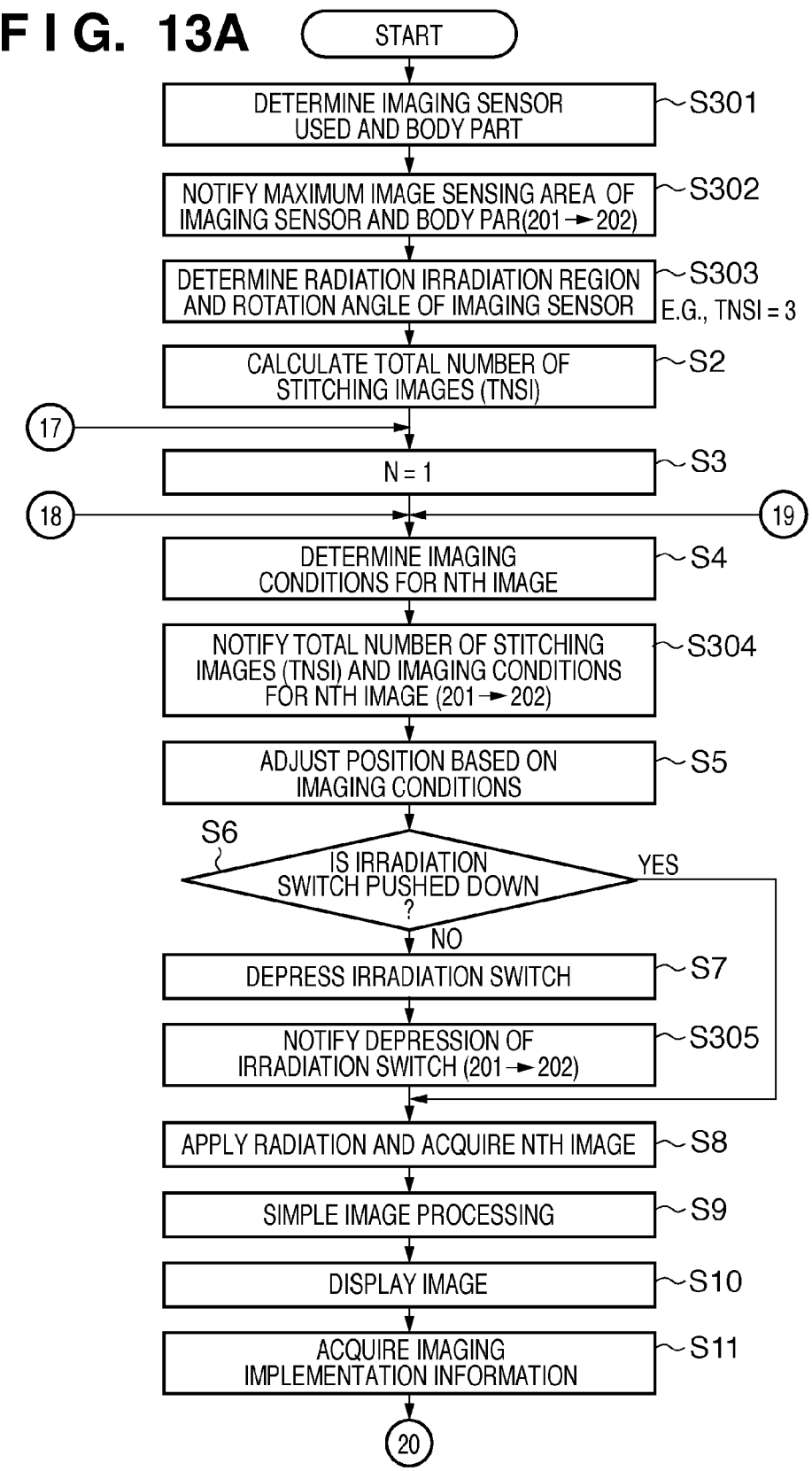

FIGS. 13A and 13B are flowcharts illustrating a flow of a divided capture method of the present invention in Embodiment 5. In FIGS. 13A and 13B, the details of the steps other than step S401 are the same as those of the steps that have been already described (for example, the steps shown in the flowcharts of FIGS. 12A and 12B), so the description thereof has been omitted here.

In step S201, the image processing unit 109 determines whether composition processing succeeds or fails. As a result, if it is determined that the processing succeeds, in step S401, the communication controller 202 sends a success notification to the communication controller 201. Through this notification, the radiation generating apparatus can know that composition processing can be performed, and the process moves to step S14 for preparation for the next imaging process.

By performing processing as described above, it is possible to determine whether composition processing succeeds or fails, even if the object has moved during imaging, or even if there is an interval between imaging processes and the object is displaced from its position in the prior imaging process.

Accordingly, it is possible to prevent a patient from undergoing unnecessary exposure to radiation or undergoing unnecessary imaging.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-120394, filed May 18, 2009 which is hereby incorporated by reference herein in its entirety.

What is claimed is:

1. A radiographic apparatus for imaging an object, comprising:
    an image capturing unit configured to capture a radiographic image of the object;
    an imaging control unit configured to control imaging performed by the image capturing unit such that series of radiographic images are captured at different aspects of the object;
    a detection unit for detecting an interruption of acquisition of the series of the radiographic images; and
    a user interface unit configured to display a user interface, when an interruption has been detected by the detection unit, for allowing a user to designate whether or not to continue an operation of acquiring the series of radiographic images.

2. The radiographic apparatus according to claim 1, further comprising:
    an irradiation switch for designating irradiation of radiation to the object,
    wherein the imaging control unit performs acquisition of the series of radiographic images while the irradiation switch is in an on-state, and,
    if the irradiation switch is brought into an off-state during acquisition of the series of radiographic images, the detection unit detects the interruption.

3. The radiographic apparatus according to claim 1, further comprising:
    an image processing unit for determining whether or not each of the series of radiographic images satisfies a specific condition for composition to form an entire image of the object,
    wherein the user interface unit allows the user to designate whether or not to continue an operation of acquiring the series of radiographic images if at least one of the series of radiographic images captured does not satisfy the specific condition.

4. The radiographic apparatus according to claim 3, wherein
    the imaging control unit counts each time when imaging is performed for the series of radiographic images,
    the image processing unit generates, when a count value obtained by the counting matches the total number of stitching images of the series of radiographic images, a composite image in which all the series of radiographic images are composed, and
    the user interface unit displays the composite image.

5. The radiographic apparatus according to claim 1, wherein
    the imaging control unit calculates the total number of stitching images required for imaging, based on information of an radiation irradiation region, of the series of radiographic images, and of a rotation angle of the image capturing unit with respect to the object.

6. The radiographic apparatus according to claim 1, further comprising:
    a radiation irradiation unit including a first communication control unit configured to send information to or receive information from the control unit; and
    a second communication control unit configured to send information to or receive information from the radiation irradiation unit.

7. The radiographic apparatus according to claim 6, wherein
    the second communication control unit notifies the first communication control unit of information relating to a maximum image sensing area of the image capturing unit and to the series of radiographic images,
    the imaging control unit determines the irradiation region of the radiation irradiation unit and the rotation angle of the image capturing unit with respect to the object based on the maximum image sensing area of the image capturing unit received by the first communication control unit, and also calculates the total number of stitching images required for imaging based on the information of the irradiation region, of the series of radiographic images, and of the rotation angle of the image capturing unit with respect to the object, and
    the first communication control unit notifies the second communication control unit of information indicating the total number of stitching images and a capturing number corresponding to each of the series of radiographic images, and an imaging condition including a rotation angle corresponding the capturing number of the image capturing unit with respect to the object.

8. The radiographic apparatus according to claim 6, wherein
    the first communication control unit notifies the second communication control unit of a result detected by the detection unit, and
    if the second communication control unit has received an interruption of acquisition of the radiographic images, the user interface unit allows the user to designate whether or not to continue an operation of acquiring the series of radiographic images.

9. The radiographic apparatus according to claim 6, wherein, if the user interface unit has received a designation of continuation from the user, the second communication control unit notifies the first communication control unit of information indicating the designation,
    the imaging control unit determines information that includes a capturing number and that is required for the next imaging, based on the information indicating the designation received by the first communication control unit, the first communication control unit notifies the second communication control unit of the information that includes a capturing number and that is required for the imaging, and the imaging control unit performs continuation of imaging in accordance with the information that includes a capturing number and that is required for the imaging.

10. The radiographic apparatus according to claim 6, wherein, if the user interface unit has received a designation of cancellation from the user, the second communication control unit notifies the first communication control unit of information indicating the designation, and the imaging control unit performs cancellation of imaging based on the information indicating the designation received by the first communication control unit.

11. The radiographic apparatus of claim 1, wherein the user interface unit displays the user interface on the display unit, if the series of the radiographic images are the images for forming a composite image of the object.

12. The radiographic apparatus of claim 1, wherein the user interface unit displays the user interface if the series of the radiographic images are captured as at least one selected from the group consisting of divided capture, long-length imaging and stitch capture.

13. The radiographic apparatus of claim 1, wherein the imaging control unit sets an imaging condition for one of the rest of the series of the radiographic images which remain to be captured if continue of the operation of acquiring the rest of the series of the radiographic image is designated via the user interface.

14. The radiographic apparatus of claim 13, wherein the image control unit sets an imaging condition, including position information of the image capturing unit, for a radiographic image which is positioned next to a radiographic image last captured, if the series of the images are to be captured as long-length imaging or stitch capture.

15. The radiographic apparatus of claim 13, wherein the imaging control unit performs preparation of image capturing corresponding to the imaging condition, in response to a designation of continue via the user interface.

16. The radiographic apparatus of claim 1 wherein the imaging control unit performs, in response to capturing of a first image of the series of the radiographic image, preparation for image capturing corresponding to an imaging condition for a second image of the rest of the series of the radiographic images determined to be captured next to the first image.

17. The radiographic apparatus of claim 1, wherein the user interface unit displays the user interface for allowing a user to designate whether or not to continue an operation of acquiring the series of radiographic images and designate whether or not to retake at least one of the captured radiographic images.

18. A method for imaging an object, comprising:
capturing a radiographic image of the object;
controlling imaging performed at capturing such that a series of radiographic images are acquired at different aspects of the object;
detecting an interruption of acquisition of the series of the radiographic images; and
displaying, when the interruption has been detected, a user interface for allowing a user to designate whether or not to continue an operation of acquiring the series of the radiographic images.

19. A radiographic apparatus adapted to imaging an object by divided capture, comprising:
an image capturing unit for capturing an image of the object;
an imaging control unit for control of imaging performed by the image capturing unit such that a plurality of captured images are acquired while switching an image sensing area for the object;
a detection unit for detecting an interruption of acquisition of the plurality of captured images performed by the image capturing unit;
a user interface unit for notifying, when an interruption has been detected by the detection unit, a user of the interruption, and for allowing the user to designate whether or not to continue an operation of acquiring the plurality of captured images; and
an irradiation switch for designating irradiation of radiation to the object,
wherein the imaging control unit performs acquisition of the plurality of captured images while the irradiation switch is in an on-state, and
if the irradiation switch is brought into an off-state during acquisition of the plurality of captured images, the detection unit detects the interruption.

20. A radiographic apparatus adapted to imaging an object by divided capture, comprising:
an image capturing unit for capturing an image of the object;
an imaging control unit for control of imaging performed by the image capturing unit such that a plurality of captured images are acquired while switching an image sensing area for the object;
a detection unit for detecting an interruption of acquisition of the plurality of captured images performed by the image capturing unit;
a user interface unit for notify, when an interruption has been detected by the detection unit, a user of the interruption, and for allowing the user to designate whether or not to continue an operation of acquiring the plurality of captured images; and
an image processing unit for determining whether or not each of the plurality of captured images satisfies a specific condition for composition to form an entire image of the object, and for determining whether or not a degree of matching between a captured image and another captured image composed with the captured image falls in a specific threshold level,
wherein the user interface unit allows the user to designate whether or not to continue an operation of acquiring the plurality of captured images if the degree of matching does not fall within the threshold level.

21. The radiographic apparatus according to claim 20, wherein
the imaging control unit counts each time when imaging is performed for the plurality of captured images,
the image processing unit generates, when a count value obtained by the counting matches the total number of stitching images of the plurality of captured images, a composite image in which all the plurality of captured images are composed, and
the user interface unit displays the composite image.

22. A radiographic apparatus adapted to imaging an object by divided capture, comprising:
an image capturing unit for capturing an image of the object;

an imaging control unit for control of imaging performed by the image capturing unit such that a plurality of captured images are acquired while switching an image sensing area for the object;

a detection unit for detecting an interruption of acquisition of the plurality of captured images performed by the image capturing unit; and a user interface unit for notifying, when an interruption has been detected by the detection unit, a user of the interruption, and for allowing the user to designate whether or not to continue an operation of acquiring the plurality of captured images, wherein the imaging control unit calculates the total number of stitching images required for imaging, based on information of an radiation irradiation region, of the plurality of captured images, and of a rotation angle of the image capturing unit with respect to the object.

23. A radiographic apparatus adapted to imaging an object by divided capture, comprising:

an image capturing unit for capturing an image of the object;

an imaging control unit for control of imaging performed by the image capturing unit such that a plurality of captured images are acquired while switching an image sensing area for the object;

a detection unit for detecting an interruption of acquisition of the plurality of captured images performed by the image capturing unit;

a user interface unit for notifying, when an interruption has been detected by the detection unit, a user of the interruption, and for allowing the user to designate whether or not to continue an operation of acquiring the plurality of captured images;

a radiation irradiation unit including a first communication control unit configured to send information to or receive information from the control unit; and a second communication control unit configured to send information to or receive information from the radiation irradiation unit, wherein the radiation irradiation unit and the imaging control unit share a status information indicating a progress of capturing of the series of the radiographic images by the first and second communication control unit.

24. The radiographic apparatus according to claim 23, wherein the plurality of captured images, a placement condition of the image capturing unit for each of the plurality of captured images, and a radiation imaging condition including a radiation irradiation region are transmitted and received between the first communication control unit and the second communication control unit.

25. The radiographic apparatus according to claim 23, wherein the second communication control unit notifies the first communication control unit of information relating to a maximum image sensing area of the image capturing unit and to the plurality of captured images, the imaging control unit determines the irradiation region of the radiation irradiation unit and the rotation angle of the image capturing unit with respect to the object based on the maximum image sensing area of the image capturing unit received by the first communication control unit, and also calculates the total number of stitching images required for imaging based on the information of the irradiation region, of the plurality of captured images, and of the rotation angle of the image capturing unit with respect to the object, and the first communication control unit notifies the second communication control unit of information indicating the total number of stitching images and a capturing number corresponding to each of the plurality of captured images, and an imaging condition including a rotation angle corresponding the capturing number of the image capturing unit with respect to the object.

26. The radiographic apparatus according to claim 23, wherein the first communication control unit notifies the second communication control unit of a result detected by the detection unit, and if the second communication control unit has received an interruption of acquisition of the captured images, the user interface unit allows the user to designate whether or not to continue an operation of acquiring the plurality of captured images.

27. The radiographic apparatus according to claim 23, wherein, if the user interface unit has received a designation of continuation from the user, the second communication control unit notifies the first communication control unit of information indicating the designation, the imaging control unit determines information that includes a capturing number and that is required for the next imaging, based on the information indicating the designation received by the first communication control unit, the first communication control unit notifies the second communication control unit of the information that includes a capturing number and that is required for the imaging, and the imaging control unit performs continuation of imaging in accordance with the information that includes a capturing number and that is required for the imaging.

28. The radiographic apparatus according to claim 23, wherein, if the user interface unit has received a designation of cancellation from the user, the second communication control unit notifies the first communication control unit of information indicating the designation, and the imaging control unit performs cancellation of imaging based on the information indicating the designation received by the first communication control unit.

* * * * *